(12) United States Patent
Stomberg et al.

(10) Patent No.: US 7,317,941 B2
(45) Date of Patent: Jan. 8, 2008

(54) TIME SYNCRHONIZATION OF DATA

(75) Inventors: Charles R. Stomberg, Forest Lake, MN (US); John M. Kruse, New Brighton, MN (US); Nancy P. Pool, Rancho Cordova, CA (US); Gregory J. Haubrich, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 696 days.

(21) Appl. No.: 10/712,905

(22) Filed: Nov. 13, 2003

(65) Prior Publication Data

US 2005/0103351 A1  May 19, 2005

(51) Int. Cl.
*A61B 5/04* (2006.01)
(52) U.S. Cl. ............................ 600/509; 128/904; 607/5
(58) Field of Classification Search ........ 128/897–899, 128/904; 600/300, 508–510; 607/2, 5, 9, 607/18, 28
See application file for complete search history.

(56) References Cited

U.S. PATENT DOCUMENTS

| | | | |
|---|---|---|---|
| 3,798,650 A | 3/1974 | McComas et al. ......... 343/225 |
| 4,316,472 A | 2/1982 | Mirowski et al. | |
| 4,375,817 A | 3/1983 | Engle et al. | |
| 4,384,585 A | 5/1983 | Zipes | |
| 4,577,633 A | 3/1986 | Berkovits et al. | |
| 4,587,970 A | 5/1986 | Holley et al. | |
| 4,633,421 A | 12/1986 | Watson, Jr. et al. | |
| 4,726,380 A | 2/1988 | Vollmann et al. | |
| 4,727,380 A | 2/1988 | Miura et al. | |
| 4,727,877 A | 3/1988 | Kallok | |
| 4,800,883 A | 1/1989 | Winstrom | |
| 4,830,006 A | 5/1989 | Haluska et al. | |
| 4,880,005 A | 11/1989 | Pless et al. | |
| 4,949,719 A | 8/1990 | Pless et al. | |
| 4,953,551 A | 9/1990 | Mehra et al. | |
| 5,117,824 A | 6/1992 | Keimel et al. | |
| 5,163,427 A | 11/1992 | Keimel | |
| 5,188,105 A | 2/1993 | Keimel | |
| 5,274,545 A | 12/1993 | Allan et al. | |
| 5,345,362 A | 9/1994 | Winkler | |
| 5,607,459 A | 3/1997 | Paul et al. ..................... 607/29 |
| 5,904,708 A | 5/1999 | Goedeke ....................... 607/18 |
| 5,921,938 A | 7/1999 | Aoyama et al. | |
| 6,041,257 A | 3/2000 | MacDuff et al. ................ 607/5 |
| 6,219,303 B1 * | 4/2001 | Morohoshi et al. ............. 368/47 |
| 2002/0038137 A1 | 3/2002 | Stein ........................... 607/46 |
| 2003/0161321 A1 * | 8/2003 | Karam et al. ........... 370/395.21 |
| 2004/0116981 A1 * | 6/2004 | Mazar ........................... 607/60 |
| 2004/0133390 A1 * | 7/2004 | Osorio et al. ................ 702/178 |
| 2004/0152958 A1 * | 8/2004 | Frei et al. ..................... 600/300 |

FOREIGN PATENT DOCUMENTS

WO    WO 92/18198    10/1992

\* cited by examiner

*Primary Examiner*—John P. Lacyk
(74) *Attorney, Agent, or Firm*—Daniel G. Chapik

(57) ABSTRACT

A device external to an implantable medical device (IMD) is provided with an accurate reference clock. The programmer receives time data from the IMD and compares that data to time data from the reference clock. Based on this comparison, the programmer determines how much a clock within the IMD is drifting per unit of time. A correction factor is generated so that data received from the IMD can then be correlated to the correct reference time.

14 Claims, 9 Drawing Sheets

TIME SYNCRHONIZATION OF DATA

FIELD OF THE INVENTION

The present invention relates to implantable medical devices. More particularly, the present invention relates to implantable medical devices that record and/or utilize a clock for time data.

DESCRIPTION OF THE RELATED ART

There are a large number of medical devices that are implanted within patients to gather data or deliver therapy. Collectively, these devices are referred to as implantable medical devices (IMDs). Such devices include, for example, cardiac pacemakers, cardioverters, defibrillators, cardiac monitors (such as the Medtronic Reveal or the Medtronic Chronicle), neural stimulators, drug pumps, muscle stimulators, nerve stimulators and the like. IMDs are also used at times, in combination with external devices, such as an external EKG. For example, an external EKG may be used to monitor a patient's heart rhythm while a pacemaker is functioning.

Certain IMDs measure data and deliver therapy within very short time intervals. For example, a typical cardiac cycle is on the order of 1 second, or 1000 milliseconds. Subelements of the cycle may be on the order of 10-50 milliseconds. Thus, the IMD is provided with a timing or clock device that facilitates precise measurement and timing along such scales. A commonly used clock circuit includes a crystal that oscillates in a predictable and relatively stable manner. Such clock circuits have proven themselves to be effective and reliable. In a typical bradycardia device, such as a pacemaker, the clock circuit includes a crystal that oscillates at 32 KHz.

While such clock circuits are reliable and sufficiently accurate when dealing with shorter time intervals, they do sometimes suffer from certain inaccuracies over longer periods of time. For example, it is known that some crystals behave differently over time. That is, as the crystals function over time, their period oscillations vary. This variance over time is, however, predictable and can be accounted for by software within the IMD. The software simply determines the length of time the crystal has been in use; compares it to a known variance curve for the crystal and implements changes to correct timing parameters for the clock circuit.

Other variances in the performance of the clock circuit, and the crystal in particular, cause discrepancies in longer-term time measurement. Again, these clock circuits are extremely accurate in the short term when, for example, measuring cardiac cycles. Over long periods of time, the clock circuit often suffers from drift, which leads to the addition of a few seconds to a few minutes over an elongated period such as a month. Thus, after a period of six months or a year, the clock circuit may be "inaccurate" on the order of many minutes, compared to a truly accurate reference. This inaccuracy is in regard to comparison to a reference time (e.g., Greenwich Mean Time (GMT)); not in regard to shorter interval measurements.

Drift generally does not affect the performance of the IMD, as the accuracy of the clock output is sufficiently great as to negate the effects of drift in the short term. That is, a clock circuit that drifts (positive or negative) a few seconds a week or month remains relatively precise over periods of seconds and minutes. It is this level of accuracy that makes IMDs reliable and functional during normal performance.

There are certain circumstances where the timing of an event that is sensed or initiated by the IMD relative to a known reference time becomes important. In those, cases drift over longer periods of time will make it difficult to correlate such an event to an appropriate frame of reference. In the case of periodic interrogation of an implantable cardioverter defibrillator (ICD), certain noteworthy medical events may be sensed and recorded and later revealed to a physician conducting the interrogation of the device. For instance, the patient may have events of tachycardia or fibrillation. The ICD will time-stamp these events; however, the time-stamp is dependant upon its own internal clock. That physician will query the patient as to what activity the patient was engaged in during the event. Thus, the time-stamp would need to relate to the patient's accurate frame of reference. The interrogations by a physician sometime only occur on yearly basis, once every two years, or perhaps even on a more infrequent basis. As such, drift could dramatically shift the time stamp. Therefore, the patient may believe the event occurred during one activity when the event actually occurred during another activity at a different time.

The problems associated with diversity between a clock in an IMD and a reference time are exacerbated when multiple IMDs are implanted within a patient and utilized in some synchronous manner. For example, a subcutaneous cardiac monitor records an EKG or EGM and time stamps the events according to an internal clock. Separately, a drug pump delivers drugs at certain intervals or in response to certain sensed events. The drug pump also records data and time stamps this data based on its own internal clock. Upon review, data from both devices is output for analysis. When these data sets are aligned, they will be aligned based on their respective time stamps. However, if one or both clocks drifted then their respective frames of reference will not coincide. When the two data sets are misaligned, the EKG may, for example, indicate a cardiac event that appears to have been caused by the delivery of the drug, when in fact, the drug was delivered in response to the cardiac event.

As such, multiple devices working in concert benefit from commonality in their timing. Furthermore, the output from multiple devices from multiple patients likewise benefit from an accurate correlation of the timing. Also, the output from a single device benefits from having data correlated to a proper frame of reference for analysis.

SUMMARY OF THE INVENTION

The present invention, in one embodiment, is a device, such as a programmer that is external to an implantable medical device (IMD). The programmer is provided with an accurate reference clock. The programmer receives time data from the IMD and compares that data to time data from the reference clock. Based on this comparison, the programmer determines how much a clock within the IMD is drifting per unit of time. A correction factor is generated so that data received from the IMD can then be correlated to the correct reference time.

The present invention includes a method comprising measuring drift of a clock within an implantable medical device. The method further includes generating a correction factor to correct for the drift.

In one embodiment, the present invention is an apparatus for correlating time data from an implantable medical device. The apparatus comprises communication means for communicating with and receiving time data from an implantable medical device and measuring means for determining an amount of drift in the time data relative to a reference time. The apparatus also includes correction means for correcting the data by removing the drift so that the corrected data correlated to the reference time.

In another embodiment, the present invention is a programmer for correlating time data from an implantable medical device to a reference time. The programmer comprises a communication link communicatively coupleable to an implantable medical device (IMD) for receiving IMD time data, a reference clock providing reference time data. The programmer also includes a calibrating module that receives the IMD time data and the reference time data, measures drift in the IMD data, and generates a correction factor.

In another embodiment, the present invention is a computer readable medium containing instructions that when executed on an electronic device causes the electronic device to perform the following functions: measuring a drift of a clock within an implantable medical device and generating a correction factor to correct for the drift.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
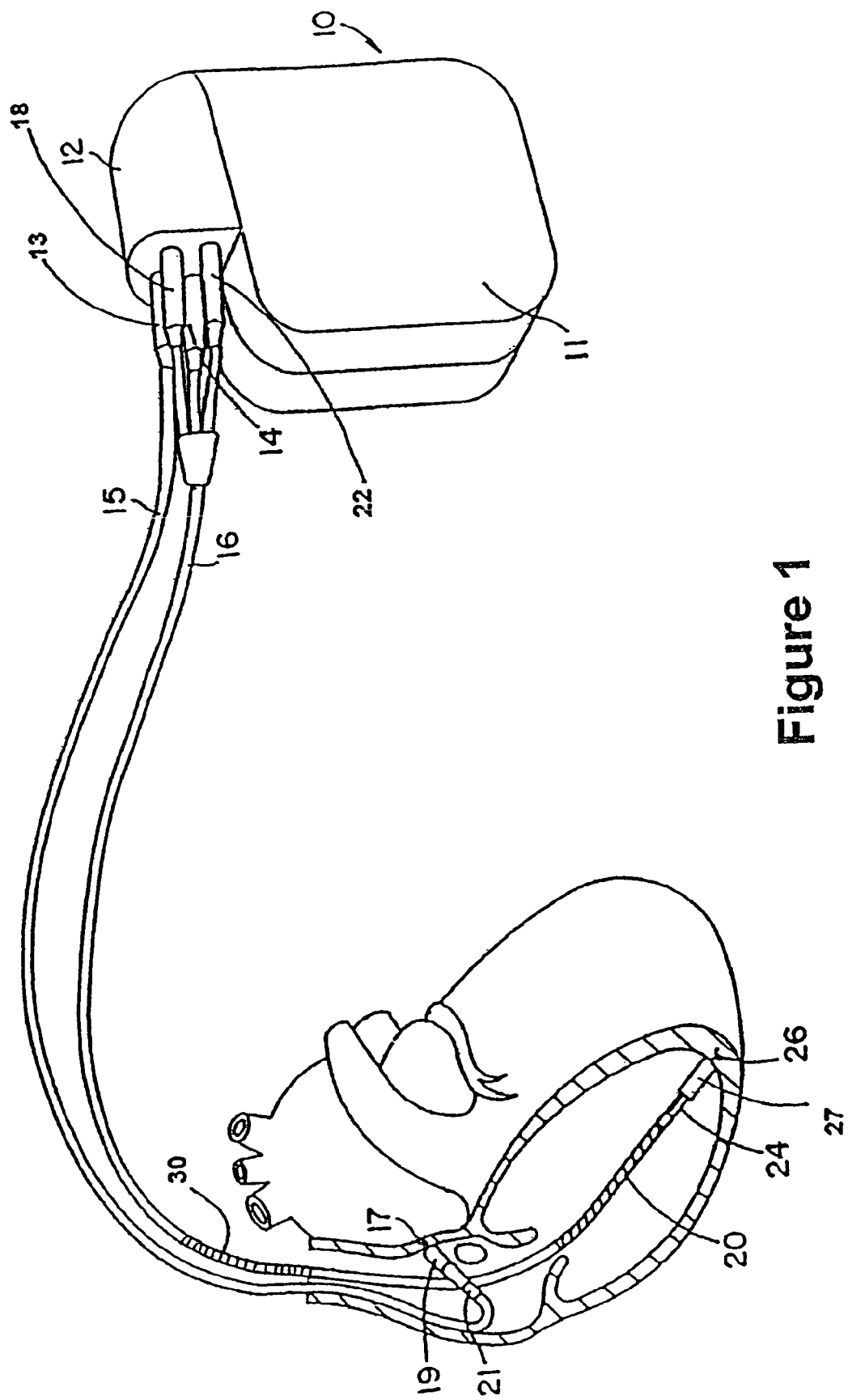
FIG. 1 is an illustration of an ICD type system according to the present invention.

Referring now to FIG. 1, there are illustrated a defibrillator 10 and leads 15 and 16, making up the ICD type system. The leads shown are illustrative, it being noted that other specific forms of leads are within the scope of this invention. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for sensing ventricular depolarizations. While electrodes 24 and 26 may be used for bipolar pacing and sensing, electrode 26 may be used in conjunction with the surface of device casing 11, which surface acts as a common or indifferent electrode in what is termed unipolar operation. Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle Lead 16 may also carry, optionally, an SCV coil 30, positioned in the subclavian vein, which can be used for R wave sensing and/or applying cardioversion pulses. Lead 16 carries respective concentric coil conductors (not shown), separated from one another by appropriate means such as tubular insulative sheaths and running the length of the lead for making electrical connection between the ICD device 10 and respective ones of electrodes 20, 24, 26 and 30.

Atrial lead 15 as illustrated includes an extendable helix electrode 17 and a ring electrode, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 10, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with the present invention.

An implantable ICD type device, or defibrillator 10, is shown in combination with atrial and ventricular leads, with the lead connector assembly 13, 14, 18, and 22 being inserted into the connector block 12 of the device 10. A specific example of a defibrillation pulse generator that may be used in conjunction with the present ventricular lead is disclosed in U.S. Pat. No. 4,953,551. Other ICD type units can be used; reference is made to U.S. Pat. Nos. 5,163,427 and 5,188,105 as disclosing illustrative forms of apparatus for delivering cardioversion and defibrillation pulses. As used herein, the term "ICD type" device refers to any device that can apply both pacing therapy and shock therapy for controlling arrhythmias.

Figure 2:
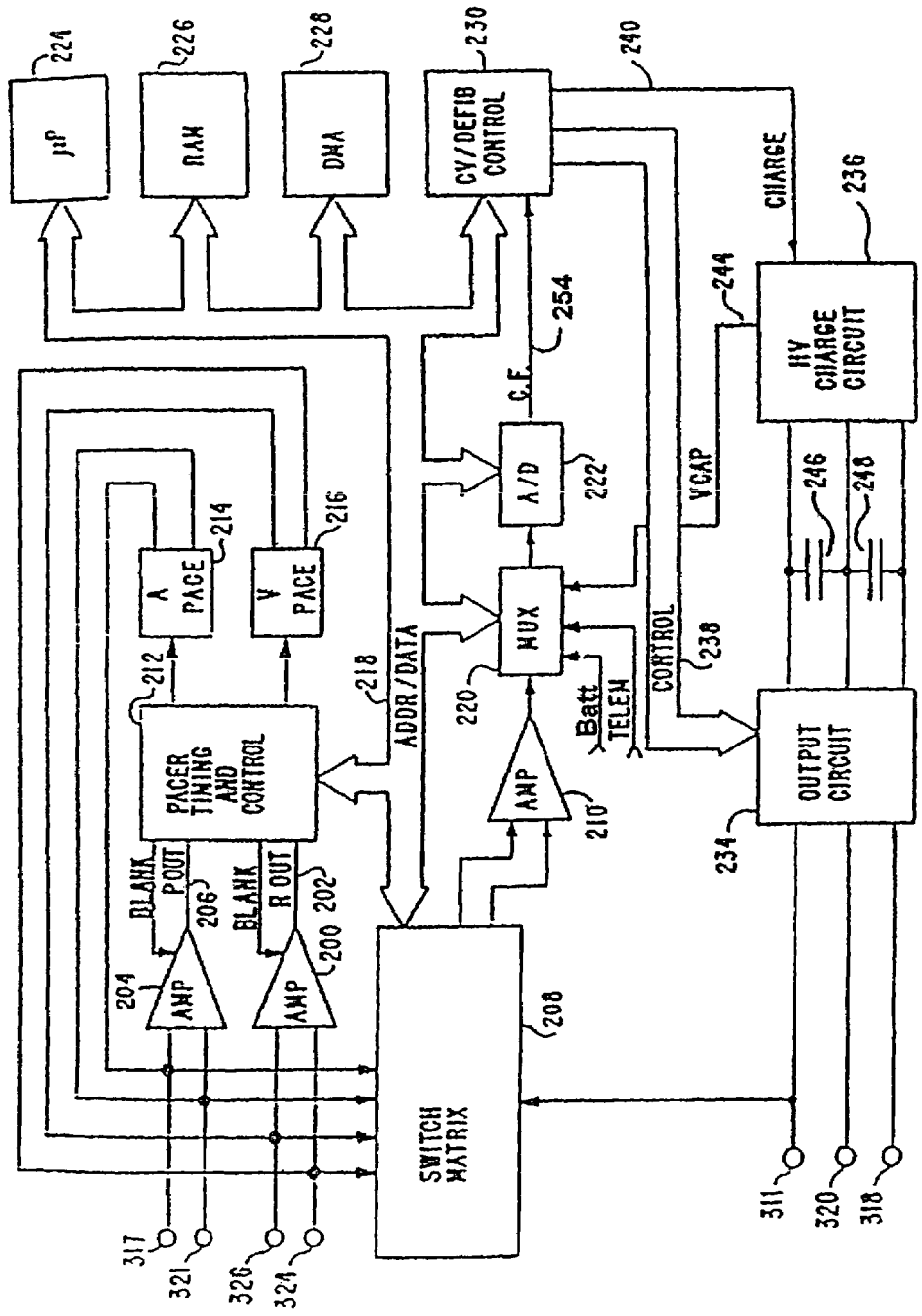
FIG. 2 is a block, functional diagram of an ICD type device adapted to carry out the features of the present invention.

FIG. 2 is a functional schematic diagram of an ICD in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implantable pacemaker/cardioverter/defibrillator. Electrode 320 corresponds to electrode 20 and is a defibrillation electrode located in the right ventricle. Electrode 318 corresponds to electrode 30 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al . . . , issued Jun. 2, 1992, for an Apparatus for Monitoring Electrical Physiologic Signals, incorporated herein by reference in its entirety.

Switch matrix 208 is used to select which of the available electrodes are coupled to wide band (0.5-200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes an electronic clock circuit and programmable digital counters that control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218.

Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the ICD may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, as discussed in the Background of the Invention section above might also be usefully employed in alternative embodiments of the ICD.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Pat. Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well.

In the event that fibrillation is identified, the typical therapy will be the delivery of a high amplitude defibrillation pulse, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
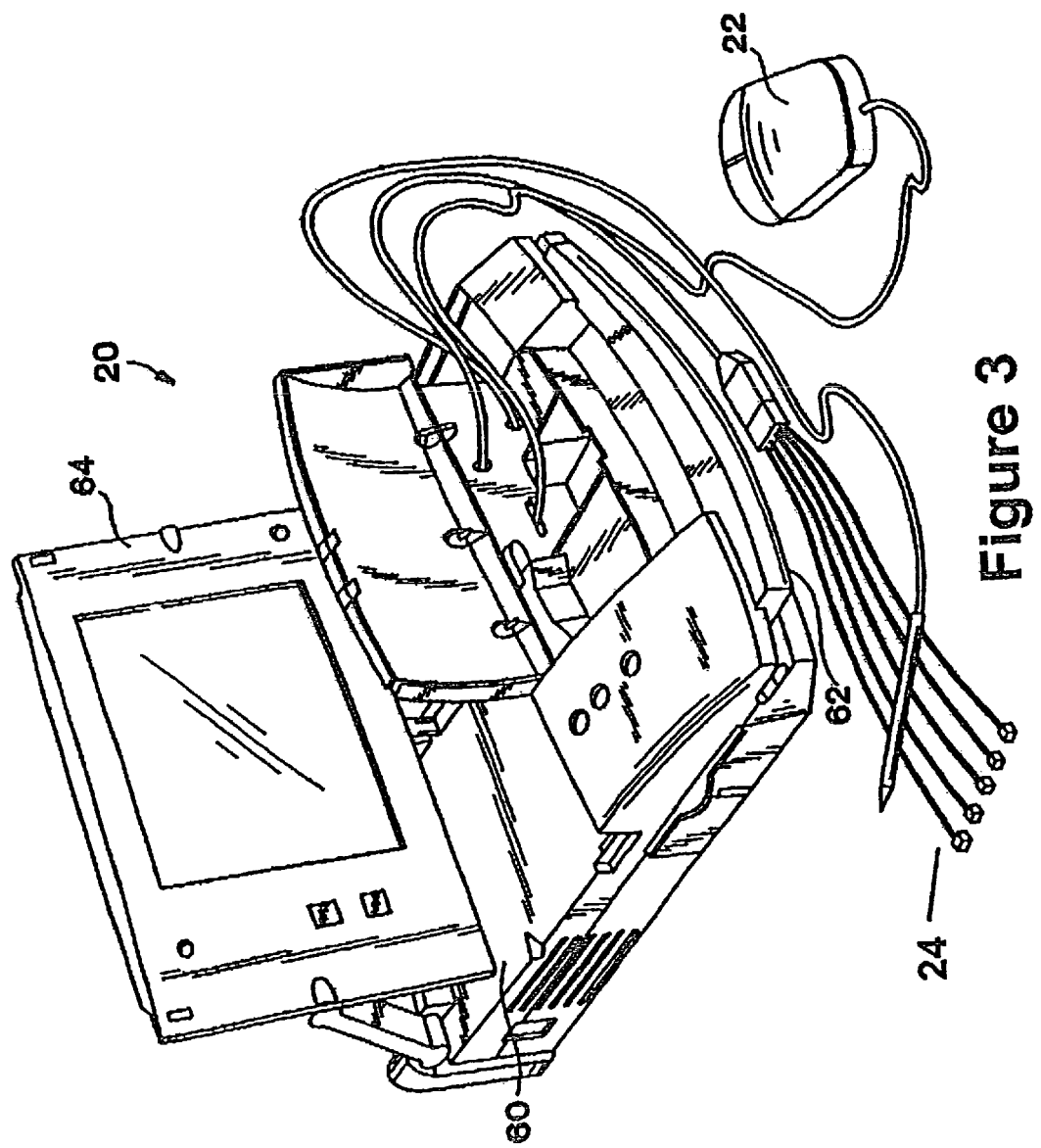
FIG. 3 is a perspective view of the external programming unit of FIG. 1.

FIG. 3 is a perspective view of a programming unit program 20 in accordance with the present invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 3, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e g., an LED, not shown) could be provided to give a visible indication of hard disk activation.

As would be appreciated by those of ordinary skill in the art, it is often desirable to provide a means for determining the status of the patient's conduction system. Normally, programmer 20 is equipped with external ECG leads 24.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety. The Medtronic Model 9790 programmer is one implantable device-programming unit with which the present invention may be advantageously practiced.

Figure 4:
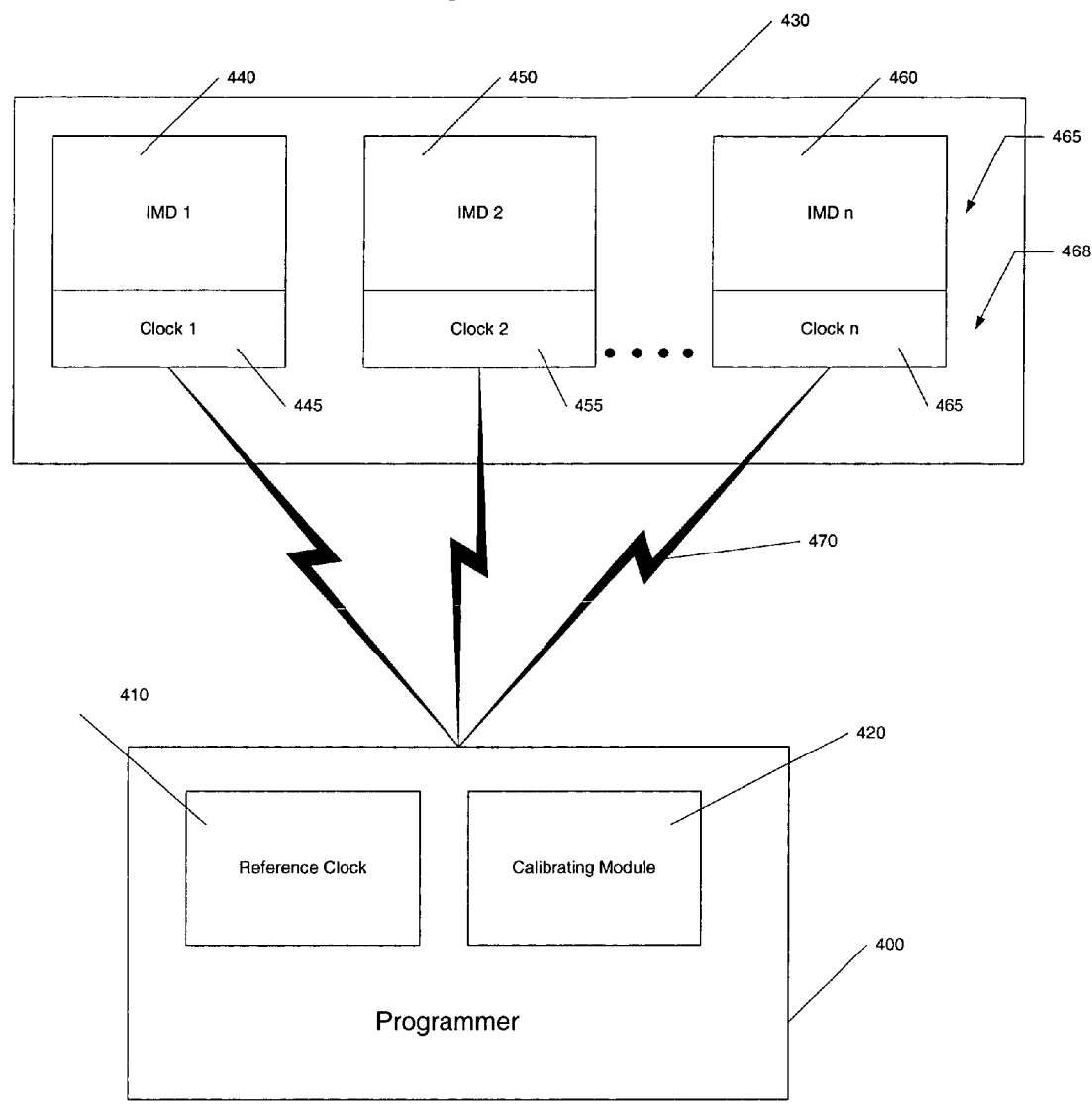
FIG. 4 is a schematic diagram illustrating a patient having multiple implanted medical devices that communicate via telemetry to an external programmer.

FIG. 4 schematically illustrates a patient 430 having an implanted medical device 440. Many patients have only a single IMD implanted, while others may have multiple devices implanted. Thus, the patient 430 is also illustrated as having IMDs 440, 450 and 460, indicative of any number of IMD implanted within a single patient 430. Collectively, one or more of these IMDs are referred to as 462.

An external programmer 400 is also illustrated. The programmer 400 is representative of an external device that collects data from one or more of the IMDs 462 implanted within the patient 430. The programmer 400 may also include certain processing features that allow the collected data to be analyzed and may include programming features that allow the programmer 400 to control one or more of the IMDs 462. For example, programmer 400 may correspond to the above-described programmer 20. Communication between the programmer 400 and an IMD 462 is facilitated through telemetry, either by placing a programming head in close physical proximity to the implanted IMD or by relying on longer-distance telemetry. In either event, communication between the IMD 465 and the programmer 400 is established.

Generally, such communication includes the uploading of device data to the programmer. Such data often includes an indication of a timeline, time stamping or various other timing related data. As previously described, certain inherent factors within clocks 445, 455, and 465 (collectively 468) lead to variations when compared to a reliable reference. Drift may cause any individual clock to gain or lose time as compared to the reference over an elongated period, usually weeks or months. Drift tends to be uniform over time; that is, if a given clock 468 gains 10 seconds in one week, it will gain 10 seconds each additional week. Lost time may result from therapy delivered by a given IMD 465. That is, certain power consuming therapies (e.g., a defibrillation pulse) may cause a loss or diminishment of power to the clock circuit. As such, the clock circuit may cease to function or function slowly for a period of time that is correlated to the therapy. Of course, the clock circuit will shortly regain power and function correctly; however, the result is a loss of time with respect to the reference clock.

As noted, a given patient 430 may have multiple IMDs 465, each having their own internal clock 468 and each such clock 468 may be affected by drift and loss of time. This tends to alter the clocks 468 time status when compared to a reference time generated by, for example, reference clock 410 in programmer 420. Furthermore, with each such individual clock 468 having generally unique variations, the clocks 468 will also vary amongst themselves.

One possible solution to these issues is to manually reset the clocks 468 during any session with an accurate reference clock. This is only a partial solution in that such a resetting generally does not result in a high level of accuracy (e.g. +/−1 minute), does not allow the stored data to be correlated, and does not address the future time discrepancies that will inevitably occur, especially when resetting occurs infrequently.

Figure 5:
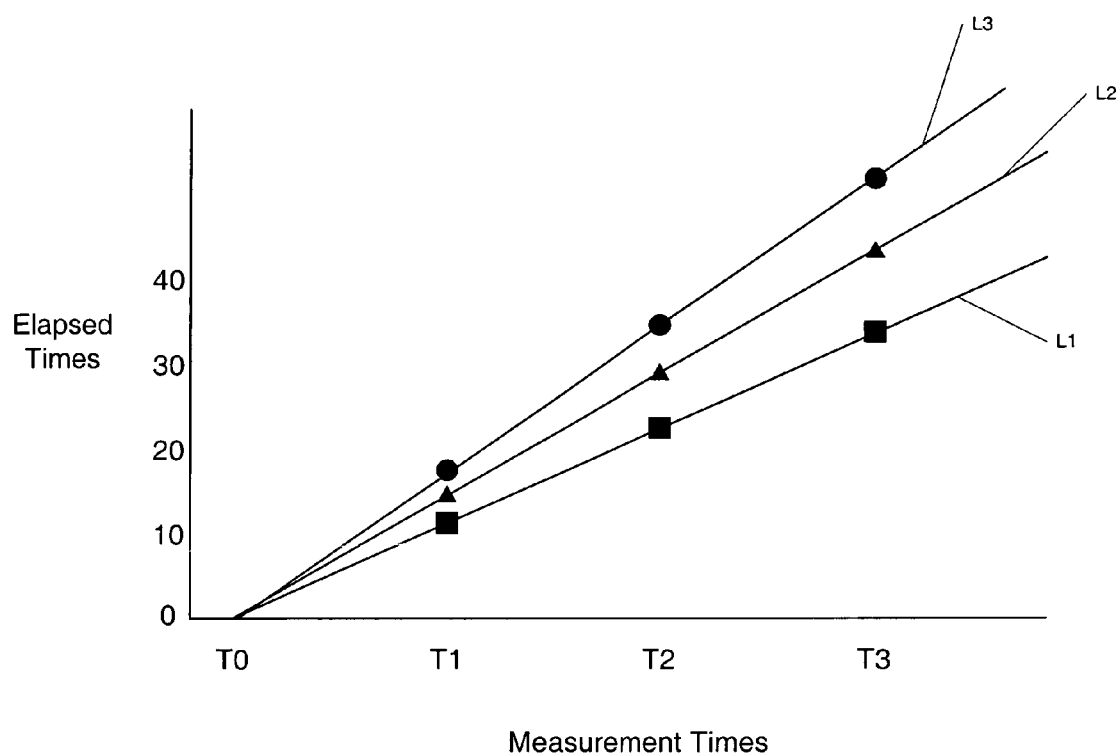
FIG. 5 is a graph illustrating the effects of drift on two time lines from devices in comparison to a reference time line.

The programmer 400 includes a calibrating module 420 to account for drift in each clock 468. In some embodiments, calibrating module 420 will also account for lost time. To account for drift, calibrating module 420 takes various data over time from the clock 468 and from the reference clock 410 while the programmer 400 is in communication with the IMD 465. This process is graphically illustrated in FIG. 5. At time T0, the process is initiated and an initial time is recorded. After some predetermined period of time has elapsed (as measured by the reference clock), a second measurement is made at time T1.

The graph illustrates the reference clock data as line L2, a first IMD data set as L1 that is loosing time and a second IMD data set L3 that is gaining time. If all of the clocks were synchronized and consistently accurate (i.e., either no drift or exactly the same drift) then their indicated times at time T1 should be identical. As there are variations indicated, that is each clock reports a different time at the reference point, drift is present. The slope of the divergence between the reference line L2 and the IMD line L1 or L3 is a measurement of drift and can be used to extrapolate a correction to the time data for any past or future point in time. The graph also illustrates additional data points at time T2 and T3, indicative of allowing a greater amount of time to elapse during the drift calibration process. As a greater amount of time elapses, the drift becomes more apparent. Of course, multiple measurements could be made and averaged.

Once the calibrating module determines the drift for a given clock 468, a correction factor is generated and utilized to correlate the time data received from the IMD 465. The correction factor may be stored within the programmer 400 and applied to data as it is received. Alternatively, the correction factor may be programmed into the IMD 465 via the programmer 400 so that subsequent data uplinked from the IMD 465 is already correlated to the reference time.

In this manner, a single clock circuit 468 within an IMD 465 is correlated to the reference clock 410 within the programmer. Using the same process in sequence or simultaneously, each clock 468 from multiple devices is so correlated. This will also have the effect of not only correlating the various clocks 468 to the reference clock 410, but will also correlate the clocks 468 to one another. Thus, drift is removed as a variable allowing events to be matched to a reference time and also allowing data from different IMDs 465 to be matched to the same accurate timeline.

Figure 6:
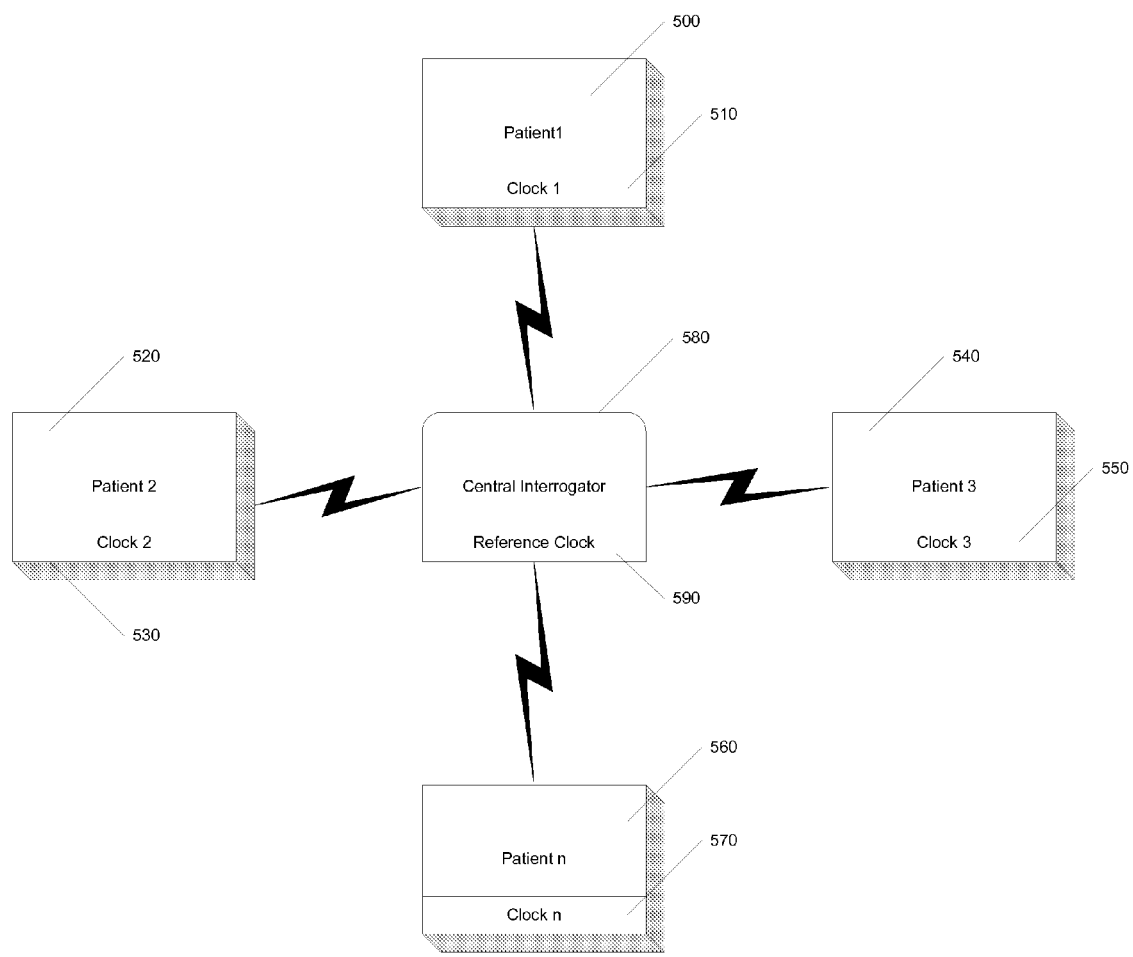
FIG. 6 is a schematic diagram illustrating multiple patients having implanted medical devices in communication with an external interrogator.

FIG. 6 illustrates a central interrogator 580 having a reference clock 590. The central interrogator may be the programmer 400 or a similar device and is intended to interrogate a plurality of patients 500, 520, 540, and 560 each having one or more IMDs, with each IMD having its own clock 510, 530, 550, and 570. By using the same processes as described above, these various clocks 510, 530, 550, and 570 can be correlated to a reference time and hence, to one another. The central interrogator 580 may be used, for example, in a clinic or hospital setting where a plurality of patients are simultaneously interrogated and their data gathered. All of this data is time adjusted to correlate with a reference time. Thus, when reviewed by a physician the data corresponds to a known time frame. In addition to implanted devices, external devices could likewise be so corrected. Furthermore, for external devices that are being used in concert with the IMD, the data from the different devices can be synchronized to a common time reference.

Figure 7:
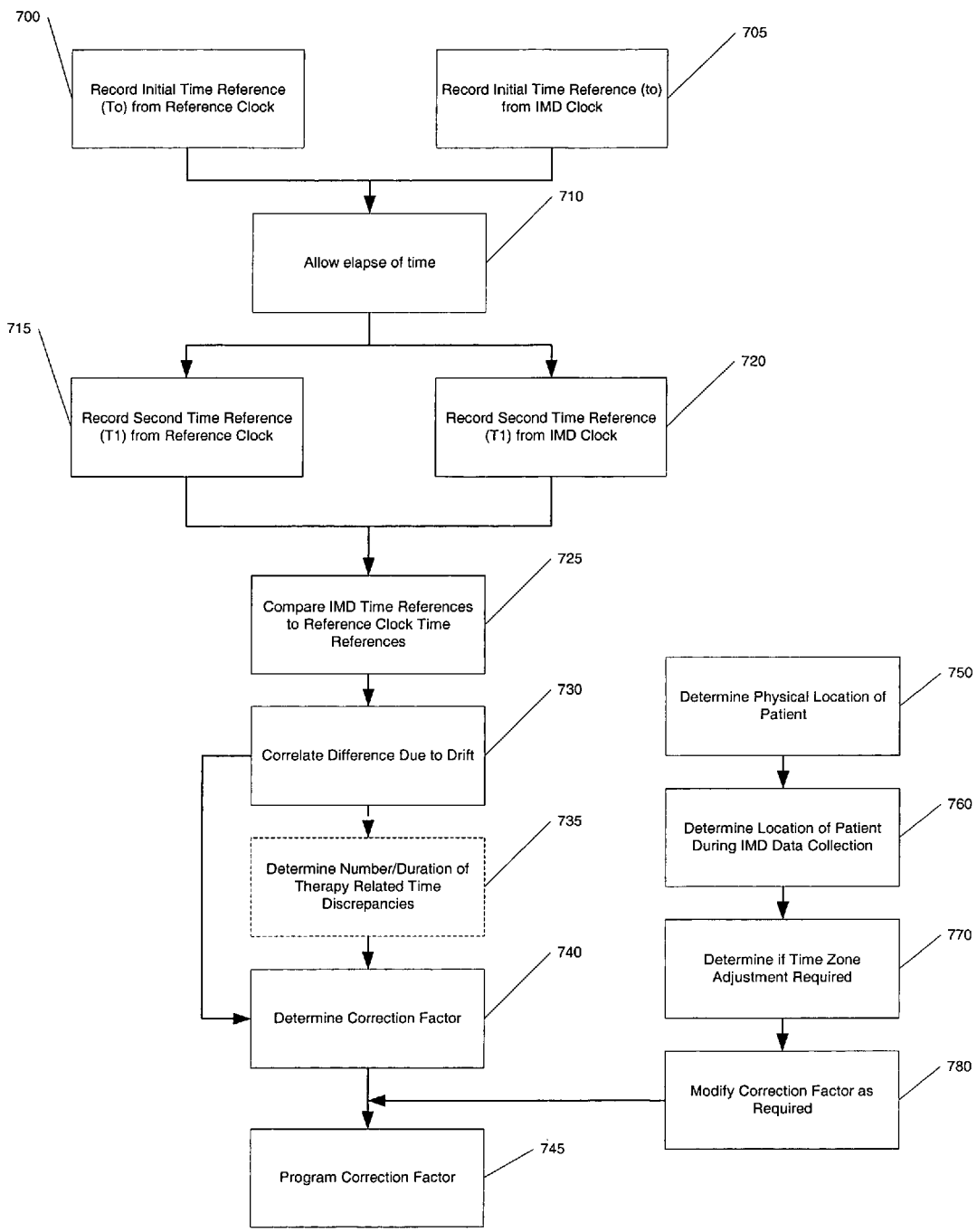
FIG. 7 is a flowchart illustrating the method of creating a correction factor.

FIG. 7 is a flowchart illustrating the method of creating a correction factor. Initially, the programmer 400, or an alternative device used to correct the IMD timing, is communicatively coupled with the IMD. Simultaneously, an initial time T0 is recorded from the reference clock (700) and the IMD clock (705). The time T0 serves as a starting point for the process. A predetermined period of time is allowed to elapse (710). The particular amount of time is selected so that the effects of drift in the IMD clock circuit produce a measurable effect. Conversely, as this process increases the amount of time the patient is being interrogated (assuming the IMD is implanted), the predetermined time should not be arbitrarily excessive.

After the predetermined period of time has elapsed, simultaneous clock outputs are recorded as T1 from reference clock (715) and the IMD clock (720). The calibrating module 420 then compares (725) the recorded data points and determines what differences, if any, exist (725). As the IMD should function normally during the interrogation, any differences should be the result of drift. That is, lost time due to therapy delivery should not be a factor in these measurements. Should therapy be delivered that could lead to lost time during this process, the calibration process should be restarted.

The calibration module 420 calculates (730) the slope of the divergence between the reference time line and the IMD time line. Thus, a correction factor is determined to mathematically correlate the IMD time line to the reference time line. That is, for any future or past point in time, the effect of drift (which is essentially constant) is calculable for the IMD time line and can be corrected. Various other algorithms could be employed to extrapolate the correlation once the data points are collected.

Once the effects of drift on the IMD clock 468 have been measured and correlated, the calibrating module 420 can determine a correction factor (740) to correct for drift. This correction factor is then programmed (745), either into the IMD 465 to affect data output or into the programmer so that data received from the IMD 465 is subsequently correlated.

In addition to correcting drift, various other time anomalies can be addressed during the process. For example, the IMD 465 often records the number and duration of therapy events. The programmer 400 can obtain (735) this data and determine how many events would lead to lost time. For example, if three 10 second events had occurred that would each have caused the clock to cease to function due to a drop in voltage, the IMD clock 468 would be offset by 30 seconds. Thus, the correction factor can be modified to include this offset as well (740). How this constant shift is implemented will depend upon how the correction factor is programmed (745). For example, if the IMD software is modified the overall correction can be made to the clocks current time (e.g., add 30 seconds to the current time). In addition, the particular lost time events can be correlated to the location within the time stream. In other words, individual adjustments (e.g., 10 seconds) are made to the IMD time data at the point in time they occurred so that subsequently occurring events are indicated at the correct time with respect to the reference. The same effect can be achieved by programming this correction factor into the programmer to correct the data as it is received from the IMD 465.

Another factor that can offset an IMD time stamp from a reference time is the physical location of the patient. That is, a difference in time zones will offset the IMD time from a reference time. Patients now have the option of having their IMD 465 interrogated remotely over the internet, telephone lines or other long distance mediums. As such, the programmer could be in a different time zone than the IMD 465 during interrogation. Similarly, the patient may travel through time zones to have their device interrogated. Finally, the patient may have traveled through different time zones during the period over which data is recorded.

To account for variations created by time zones, the present physical location of the patient is determined (750). If the patient's location is the same as the programmer's location, there is no discrepancy. If they are located in different time zones, the time zone shift is noted. Subsequently, the physical location of the patient during the period of data collection for the IMD 465 is determined (760). Again, if time zones changes occurred, the amount of shift is noted. To make these determinations, any number of mechanisms may be utilized. The simplest is to simply ask the patient their current location, if they have spent time in other times zones and if so, the date. Automated means such as incorporating a GPS unit into the IMD 465 could also be used.

Once the time zone data has been collected, a determination is made (770) as to whether a correction is required. If so, a time zone correction factor is generated and used to modify the overall correction factor (780). The nature of the correction will depend on which time zone parameters were found. For example, if the reference clock and the current IMD location are different, a constant can simply be added or subtracted to the data or to the reference time. As this is primarily a data analysis tool, this correction would not likely be used to permanently modify the IMD 465. If certain portions of the IMD data were collected in diverse time zones, then those data segments will be shifted by the appropriate constant. Again, this is used to modify the data and generally would not be used to alter the programming of the IMD 465. For individual patients, correcting shifts in time zones is to allow the patient to recall what activities were occurring based on accurate times. For example, a patient may go to sleep at 10:00 p.m. every night. Data may include an event occurs at 8:00 p.m. Without the correction, the patient will be queried about the wrong time period because of time zone differences.

Figure 8:
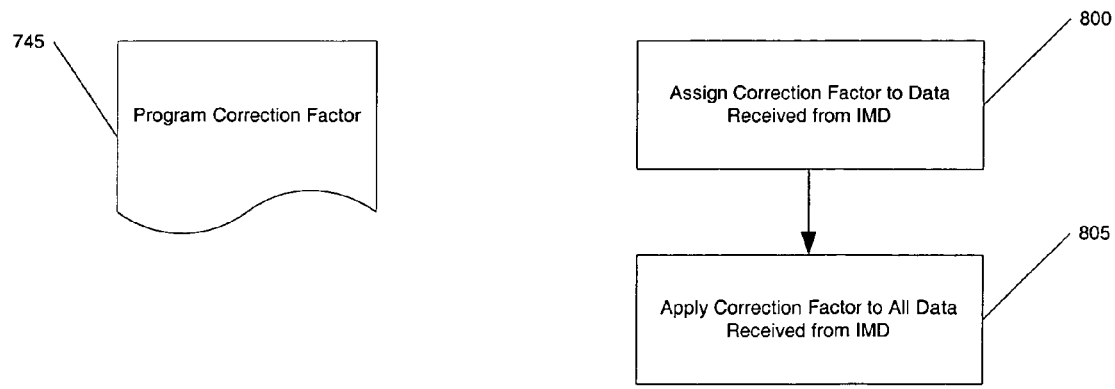
FIG. 8 is a flowchart illustrating a first method for programming the correction factor.

FIG. 8 illustrates one method of implementing the correction factor (745). Here, the data is received uncorrected/ unmodified from the IMD 465. Once received within the programmer 400, the proper correction factor(s) is identified (800). The correction factor is either identified from an earlier interrogation session or from a time correlation (e.g., FIG. 7) that was just performed for the IMD 465. For example, if the only effect monitored is drift, the correlation could be done at the first interrogation session and the correction factor could then be utilized for subsequent interrogations. Performing the calibration with each interrogation allows for various other factors to be monitored and would also note variations in drift, should they occur.

Once the correction factor is identified, it is applied (805) to the data within the programmer 400. Specifically, one or more of the following occur: each time marker is adjusted based on the drift measurement previously made; lost time is accounted for in context; and time zone shifts are corrected.

Figure 9:
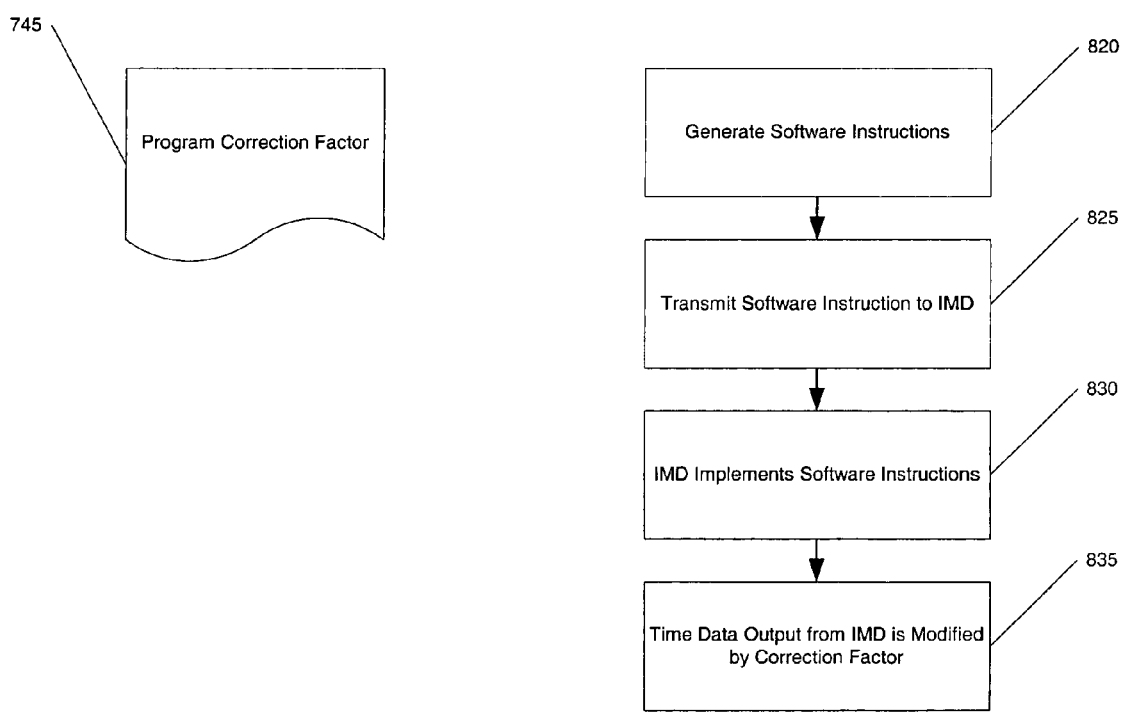
FIG. 9 is a flowchart illustrating a second method for programming the correction factor.

FIG. 9 illustrates another method of programming the correction factor (745). After the various measurements via the programmer are taken to determine what the correction factor(s) is, software instructions are generated (820) to modify the IMD. These instructions are sent (825) to the IMD (465) where they are accepted and implemented (830). Any time data then subsequently sent out from the IMD (465) is modified (835) by the software instructions. For example, while drift still occurs, it is the software within the IMD (465) that correlates the time data to the reference time based on the correction factor. Likewise, lost time is accounted for within the IMD (465) as are time zone shifts. The IMD output will subsequently be corrected for drift (assuming constant drift). It is also possible to implement a correction for lost time wherein the IMD adds a predetermined amount of time, in sequence, each time specific therapies are delivered that lower the voltage to the clock circuit. This would be based on an understanding of how much time is lost based on each type of event, which could be measured during the correlation process. Generally, time zone shifts will be corrected during interrogation unless the IMD is provided with a GPS or similar system.

Figure 10:
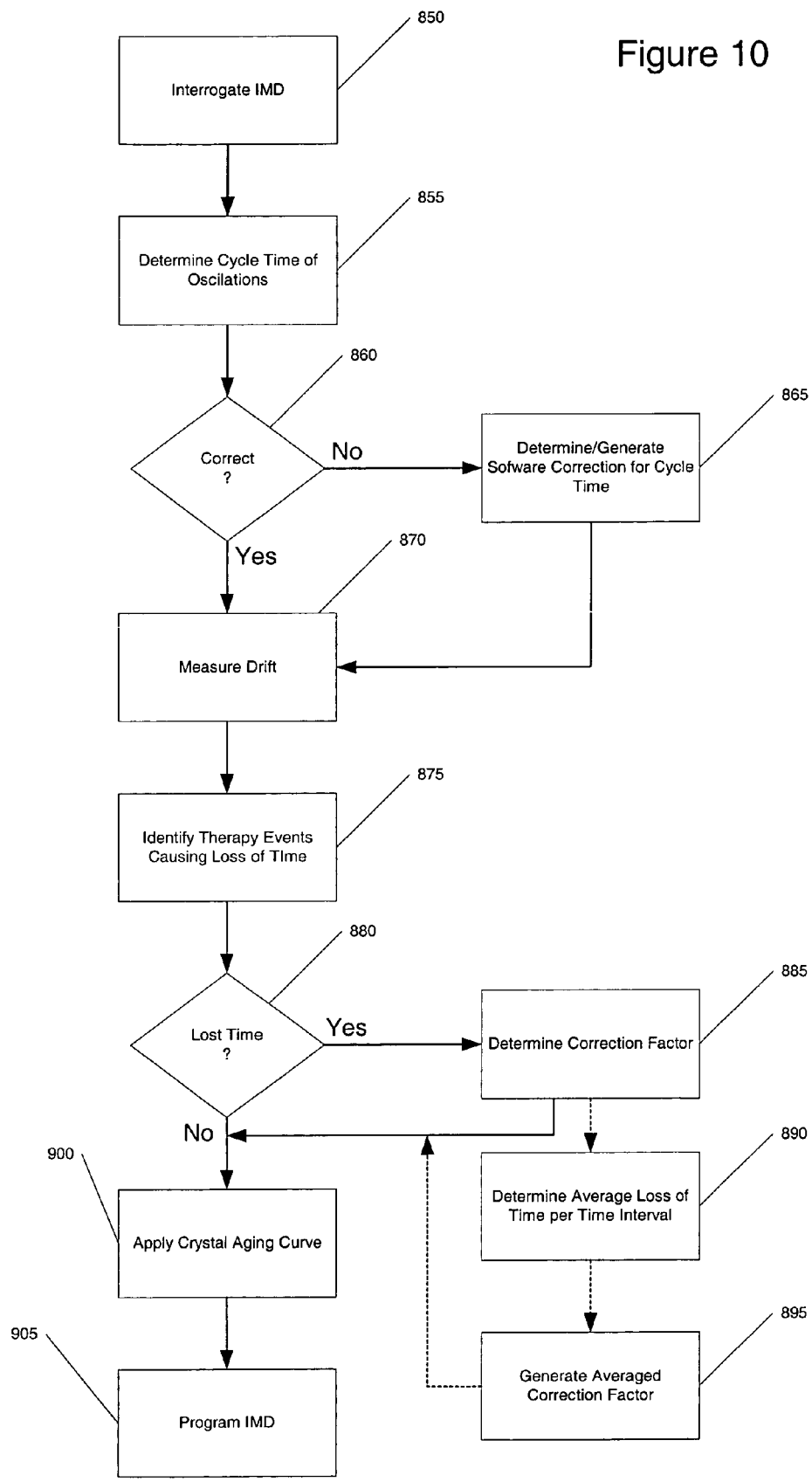
FIG. 10 is a flowchart illustrating a method of programming an IMD to adjust for time discrepancies from an internal clock.

FIG. 10 is a flowchart illustrating a method of programming the IMD 465 to adjust for time discrepancies from an internal clock 465. The IMD 465 is communicatively coupled with a programmer or similar device and the IMD is interrogated (850). The clock circuit 468 of the IMD 465 typically utilizes a crystal (or some other oscillator) that oscillates at a predetermined rate. While generally similar, individual oscillators may have variances. As the oscillation defines the fundamental time measuring interval for the circuit, these variances should be corrected. Typically, this is done during manufacturing. The IMD 465 is tested and the particular oscillation frequency is measured. A software instruction is programmed that correlates the particular oscillation frequency to standard time intervals. This is generally a one-time correction; however, as it requires some time to complete it slows the manufacturing process thereby increasing manufacturing costs.

The present invention provides a function to make this fundamental correlation, thus removing this step from the manufacturing process. Thus, after the IMD 465 is communicatively coupled with the programmer, the IMD 465 is interrogated (850) and the frequency of the oscillator is measured. If the frequency is correct, the process proceeds. However, if the frequency varies from the norm, the programmer 400 determines (865) what correction factor is required to correlate the given frequency with standard units of time. This correction factor must be programmed into the IMD and that may occur at this point, or with the other correction factors described below.

The correction factor for the oscillator frequency is generally a one-time measurement and correction. As such, steps (855), (860) and (965) can be performed once during an initial interrogation. Alternatively, these steps can be repeated during each interrogation to account for any changes that may occur to the oscillator. Preferably, the IMD 465 is interrogated and programmed according to this aspect of the present invention prior to implantation in a patient.

Once the oscillator correction factor is determined (or bypassed), drift is measured (870), in the manner previously described. Lost time (if any) is identified based on the occurrence of therapies that would cause the voltage to the clock circuit to be lowered to a point where the clock circuit slows significantly or provides no output. Thus, such therapy events are identified (875). At (880), a determination is made if time was lost. If so, a correction factor is determined (885) as previously described. Optionally, the correction factor could include a predictive model that relies on averaged therapy data. Specifically, an average amount of time lost over a given period is determined (890) and an averaged correction factor is generated (895). This correction factor can be programmed into the IMD 465 in an effort to average out lost time and bring the time data output from the IMD 465 closer to the reference time. Of course, a more accurate method involves the IMD 465 adding the actual lost time to its own data each time such a therapy is delivered.

At (900) the aging curve for the crystal is applied. As previously mentioned, oscillators and crystal in particular change in a known manner over time. Thus, based on the time of use of the oscillator and measurements made over time, a generalized correction can be made based on this curve.

After the various correction factors have been determined, this information is then programmed (905) into the IMD. While this can be done in a single step, each specific correction factor could be programmed into the IMD 465 as each correction factor is determined within the process. Thus, the IMD 465 is programmed to correlate the frequency of the oscillator to standard time measurements and to implement the aging curve. These two correction factors are static and can be done initially, without requiring patient data. The correction factor for drift is likewise implemented. Drift can me measured regardless of patient data, so long as a sufficient detection period is provided so that drift is measureable. The correction factor for lost time is only relevant when the device is functioning. That is, lost time only occurs when therapy is delivered (actual or test) or other energy draining events occur.

In an alternative embodiment, the telemetry transmission frequency is determined and compared with an expected value. Any variation from the expected value will be indicative of a variation in the oscillator relied on for transmitting. With reference back to FIG. 4, the IMD 440, for example, has established the communication link 470 via telemetry. By determining which frequency the IMD 440 is transmitting at, the IMD 440 is able to determine if a variation in the oscillator is present.

In order for such a determination to be relevant to time correlation, the same oscillator that is used for telemetry would also be used for the clock 445 and the various timing functions and such is the case in some embodiments. When the same oscillator is used for both functions, the shift in the transmission frequency can be correlated to drift in timing; thus, the data can be corrected for in much the same manner as previously described.

The identification of variations based on frequency measurements can be used alone or in combination with the previously described drift calculations. In one embodiment, drift is measured through a comparison of timing data at one interrogation and then the frequency measurements are made during subsequent interrogations. In summary, when the same oscillator is used for both telemetry and timing, changes in that oscillator will affect both functions. Thus, by measuring changes in the transmission frequency, the changes to the oscillator are determinable. Once those changes are determined, they are correlated to the effect they will produce on timing and therefore, subsequent timing data can be corrected.

Although the present invention has been described with reference to preferred embodiments, persons skilled in the art will recognize that changes may be made in form and detail without departing from the spirit and scope of the invention.

The invention claimed is:

1. A method comprising:
   measuring drift of a clock within an implantable medical device; and
   generating a correction factor to correct for the drift;
   detecting a first time output from the clock of the implantable medical device at a first time;
   detecting a first time output from a reference clock at the first time;
   detecting a second time output from the clock of the implantable medical device at a second time;
   detecting a second time output from the reference clock; and
   calculating the drift based on the difference between the second time output from the clock of the implantable medical device and the second time output from the reference clock, wherein calculating the drift includes determining a slope of a divergence between a first timeline defined between the first time and the second time for the clock of the implantable medical device and a second time line defined between the first time and the second time for the reference clock.

2. The method of claim 1, further comprising:
   correlating time data from the clock to a reference time frame by correcting for the drift.

3. The method of claim 2, wherein the time data is received at a programmer and then correlated.

4. The method of claim 1, further comprising:
   programming the implantable medical device with the correction factor.

5. The method of claim 1, further comprising:
   identifying lost time; and
   correcting the lost time.

6. The method of claim 5, wherein identifying lost time includes identifying periods of therapy delivery.

7. The method of claim 5, wherein correcting includes modifying data from the IMD so that the lost time is added back to the data temporally proximate where the time was lost.

8. An apparatus for correlating time data from an implantable medical device comprising:
   communication means for communicating with and receiving time data from an implantable medical device;
   measuring means for determining an amount of drift in the time data relative to a reference time;
   correction means for correcting the data by removing the drift so that the corrected data correlates to the reference time;
   means for determining differences between the time data and the reference time due to time zone variations; and
   means for modifying the time data to eliminate the differences due to time zone variations.

9. The apparatus of claim 8, further comprising:
   means for determining lost time; and
   means for correcting for the lost time.

10. The apparatus of claim 8, further comprising:
    measuring means for measuring a frequency of an oscillator within a clock circuit of the implantable medical device; and
    programming means for generating a correction factor to correlate the frequency to a standard time format.

11. The apparatus of claim 8, further comprising means for simultaneously synchronizing time data from multiple implantable medical devices to the reference time.

12. A computer readable medium containing instructions that when executed on an electronic device cause the electronic device to perform the following functions:
    measuring a drift of a clock within an implantable medical device by
        detecting a first time output from the clock of the implantable medical device at a first time;
        detecting a first time output from a reference clock at the first time;
        detecting a second time output from the clock of the implantable medical device at a second time;
        detecting a second time output from the reference clock; and
        calculating the drift based on the difference between the second time output from the clock of the implantable medical device and the second time output from the reference clock and determining a slope of a divergence between a first timeline defined between the first time and the second time for the clock of the implantable medical device and a second time line defined between the first time and the second time for the reference clock; and
    generating a correction factor to correct for the drift.

13. The medium of claim 12, further including correlating time data from the clock to a reference time frame by correcting for the drift.

14. The medium of claim 12, wherein the instructions cause the electronic device to program the implantable medical device with a correction factor that corrects for the drift.

* * * * *